US00PP30533P2

(12) United States Plant Patent
Korlipara

(10) Patent No.: US PP30,533 P2
(45) Date of Patent: May 21, 2019

(54) ***PENSTEMON* PLANT NAMED 'TNPENDV'**

(50) Latin Name: ***Penstemon* hybrid**
Varietal Denomination: TNPENDV

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,827

(22) Filed: Apr. 30, 2018

(51) Int. Cl.
*A01H 6/68* (2018.01)
*A01H 5/02* (2018.01)

(52) U.S. Cl.
USPC ..... Plt./465
CPC ..... *A01H 6/68* (2018.05); *A01H 5/02* (2013.01)

(58) Field of Classification Search
USPC ..... Plt./465
CPC ..... A01H 5/02
See application file for complete search history.

*Primary Examiner* — Kent L Bell
(74) *Attorney, Agent, or Firm* — Klarquist Sparkman, LLP

(57) ABSTRACT

A new and distinct cultivar of *Penstemon* plant characterized by dark green leaves, tinted purple with winter temperatures, lavender to violet flowers, short, a compact, upright and well branched habit, attractive deep purple seed heads, and excellent vigor.

1 Drawing Sheet

Botanical denomination: *Penstemon* hybrid.
Variety designation: 'TNPENDV'.
Trademark designation: Dakota™ Verde

BACKGROUND OF THE INVENTION

The present invention relates to a new and distinct cultivar of *Penstemon*, given the name, 'TNPENDV'. *Penstemon* is in the family Plantaginaceae (formerly Scrophulariaceae). This plant originated in a controlled breeding plan to create a compact series with good flowering. The parents are unknown, unnamed proprietary plants. This cultivar was selected for its green foliage, short habit, bi-color flowers, hardiness, and vigor. It is an ideal plant for a sunny border in full sun.

The trademark designation for this variety is Dakota™ Verde.

Compared to plants of *Penstemon digitalis*, an unpatented plant, the new cultivar is shorter and more compact, flowers are more lavender to violet rather than white and foliage color that is tinted purple with winter temperatures rather than green.

Compared to plants of *Penstemon digitalis* 'Mystica', an unpatented seed strain, the new cultivar is shorter and more compact, flowers are more lavender to violet than white and the foliage is green rather than dark purple.

Compared to *Penstemon* 'Dark Towers', U.S. Plant Pat. No. 20,013, the new cultivar has a shorter and more compact habit, flowers are more lavender to violet rather than pink and the foliage is green rather than dark purple.

Compared to *Penstemon digitalis* 'TNPENDB', U.S. Plant patent application Ser. No. 15/932,828, the new cultivar has green leaves rather than dark purple.

*Penstemon* 'TNPENDV' is uniquely distinguished by its:

1. dark green leaves, tinted purple with winter temperatures,
2. lavender to violet flowers, 3. short, compact, upright and well branched habit,
4. attractive deep purple seed heads, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar as a six-month-old plant growing in the trial field in mid-August in Canby, Oreg.

FIG. 2 shows the dark purple foliage of the new cultivar as a nine-month-old specimen after cold temperatures in the trial field in November in Canby, Oreg.

DETAILED PLANT DESCRIPTION

The following is a detailed description of the new *Penstemon* cultivar based on observations of eight-month-old specimens grown outside in the trial field in full sun in Canby, Oreg. in August. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, 5$^{th}$ edition, 2007.

Plant:

*Type*.—Herbaceous perennial, semi-evergreen (evergreen in USDA Zone 8).

*Form*.—Upright, basal clump, with 6 to 8 leafy flowering stems from base.
*Size*.—Grows to 50 cm wide and 53 cm tall to top of inflorescence.
*Crown count number*.—15.
*Roots*.—Fibrous, with many downward growing and a few laterals, ivory in color, Yellow White 158D, roots develop easily from cuttings from the crown.
*Vigor*.—Excellent.
*Cold hardiness*.—USDA Zone 3.

Leaf (basal):
*Type*.—Simple.
*Arrangement*.—Rosette.
*Shape*.—Lanceolate.
*Venation*.—Pinnate.
*Margins*.—Serrulate.
*Apex*.—Acute.
*Base*.—Attenuate.
*Blade size*.—Grows to 13 cm long and 4.4 cm wide.
*Surface texture*.—Both sides glabrous.
*Petiole*.—Petiole clasping, to 9.3 cm long and up to 6 mm wide.
*Leaf color*.—Topside closest to Green 139A with veins Green 139B, bottom side Green 137C with veins Green 137B, sustained cold temperatures tint leaves Greyed Purple N186B.

Leaf (stem):
*Type*.—Simple.
*Habit*.—Upright.
*Arrangement*.—Opposite, clasping.
*Shape*.—Lanceolate.
*Venation*.—Pinnate, top and bottom Green 137C.
*Margins*.—Serrate, sustained cold temperatures tint margins Greyed Purple N186B.
*Apex*.—Acute.
*Base*.—Attenuate.
*Blade size*.—Grows to 9.1 cm long and 3 cm wide.
*Surface texture*.—Glabrous on both sides.
*Petiole*.—Up to 7 mm, Greyed Purple 187A.
*Leaf color*.—Topside Green 137B, bottom side Green 137C.
*Stem*.—Upright, 30 cm long and 6 mm to 10 mm wide (at the base), glabrous at base to glandular pubescent toward rachis, internodes grow to 5.3 cm long, Greyed Purple 187A.

Inflorescence:
*Type*.—Terminal, many flowered, loose thyrse.
*Number of flowers per inflorescence*.—75 to 100.
*Rachis size*.—15 cm long and 4 cm wide, sparsely pubescent, Greyed Purple 187A.
*Peduncle*.—Grows to 7 cm long and 5 mm wide, pubescent, Greyed Purple 187A.
*Pedicel*.—Grows to 4 mm long and 1 mm wide, pubescent, Greyed Purple 187A.
*Bloom period*.—June to frost in Canby, Oreg.

Flower bud:
*Size*.—2.6 cm long and to 8 mm wide.
*Description*.—Closed tubular.
*Color*.—Tips of corolla Purple N78C blending to White NN155B.

Flower:
*Type*.—Zygomorphic, perfect.
*Shape*.—Tubular, bilabiate.
*Size*.—Grows to 3.5 cm long and 1.5 cm wide.
*Corolla description*.—Grows to 3.2 cm long and 1.5 cm wide; tube is bulbous in the calyx for 5 mm long and 3 mm wide, narrowing for 2 mm, then widening for 2.5 cm and flaring to 1.5 cm wide, 5 lobes, the two smaller top lobes flare back (each 6 mm wide and to 7 mm deep) and two larger lateral lobes curl back slightly (9 mm wide and 8 mm deep), and the lower lobe flares back slightly (7 mm wide and 6 mm deep), lobe margins entire, tips acute; outside glandular pubescent, inside pubescent; outside color bulbous section Purple 76A on top, Purple 76C bottom, inside color lobes and bulbous section White N155B, tube Red Purple 72B with bee tracks Red Purple 72A.
*Calyx description*.—5 mm deep and 9 mm wide, 5 lobes, each lobe ovate in shape, 4.5 mm long and 4 mm wide, margins entire, tip acuminate, base cuneate, both sides between Greyed Purple N187A and Greyed Purple 187A, both sides pubescent.
*Pistil description*.—1, 2.4 cm long, ovary 7 mm long and 2 mm wide, Green 143C; style 2 cm long and less than 1 mm wide, White NN155C, stigma Purple 77A.
*Stamen description*.—5, one sterile without an anther, held within the corolla 2.2 cm long, filaments 2 mm long and White NN155B, anthers 2 mm long, Brown N200B, pollen White NN155C.
*Pollen*.—Scarce.
*Fragrance*.—None.
*Lastingness*.—A flower lasts 5 to 6 days.

Fruit:
*Type*.—Capsule.
*Fertility*.—Fair.
*Size*.—10 mm deep and 6 mm wide.
*Shape*.—Conical.
*Color*.—Greyed Purple 187A.

Seed:
*Shape*.—Irregular.
*Size*.—2 mm long.
*Color*.—Black 202A.

Pests and diseases: The new cultivar is typical to the genus. No problems have been found in Canby, Oreg.

I claim:

1. A new and distinct cultivar of *Penstemon* plant substantially as illustrated and described herein.

* * * * *

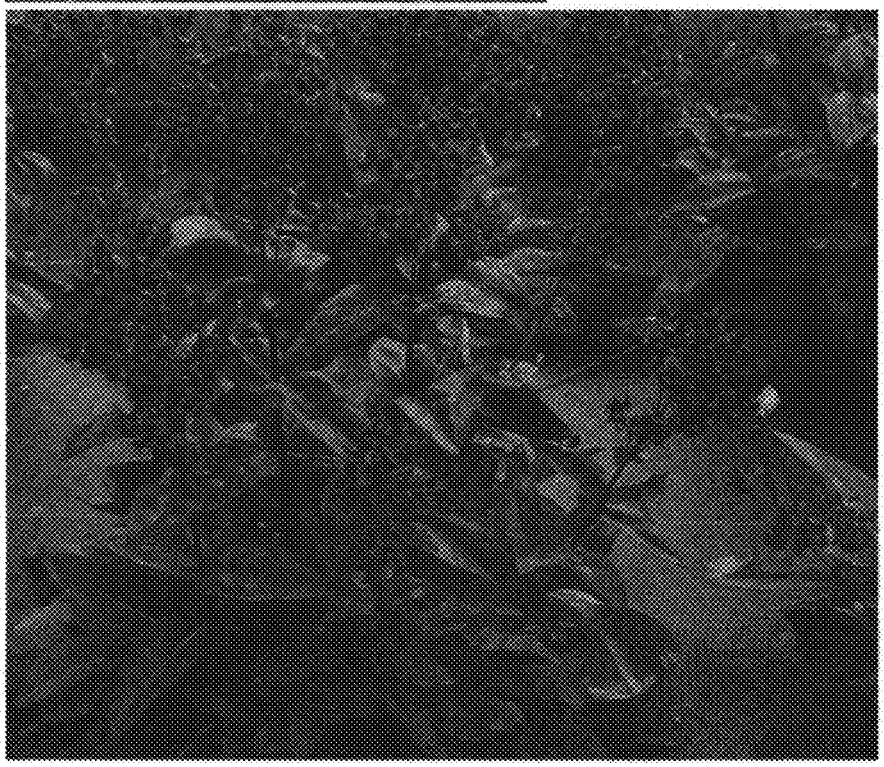

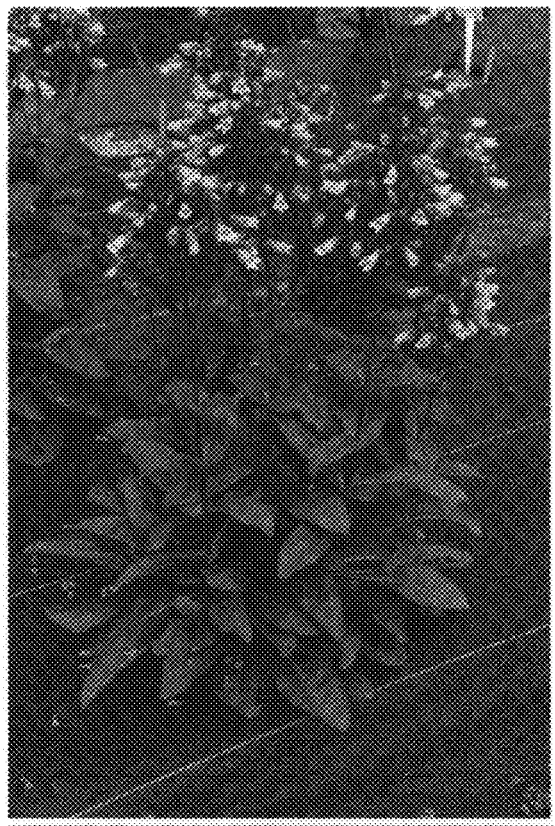
FIG. 1 Left
FIG. 2 Below